(12) United States Patent
Triolo et al.

(10) Patent No.: US 11,419,772 B2
(45) Date of Patent: Aug. 23, 2022

(54) WHEELCHAIR SYSTEM WITH MOTION SENSORS AND NEURAL STIMULATION

(71) Applicant: The United States Government as represented by The Department of Veterans Affairs, Washington, DC (US)

(72) Inventors: Ronald J. Triolo, Cleveland Heights, OH (US); Stephanie Bailey, Shaker Heights, OH (US); Kevin M. Foglyano, Lakewood, OH (US); Kiley Armstrong, Sylvania, OH (US); Musa L. Audu, Shaker Heights, OH (US)

(73) Assignee: United States Government as represented by the Department of Veterans Affairs, Washington, DC (US)

( * ) Notice: Subject to any disclaimer, the term of this patent is extended or adjusted under 35 U.S.C. 154(b) by 663 days.

(21) Appl. No.: 16/056,631

(22) Filed: Aug. 7, 2018

(65) Prior Publication Data
US 2019/0038484 A1 Feb. 7, 2019

Related U.S. Application Data

(60) Provisional application No. 62/541,879, filed on Aug. 7, 2017.

(51) Int. Cl.
*A61G 5/02* (2006.01)
*A61G 5/10* (2006.01)
(Continued)

(52) U.S. Cl.
CPC ............. *A61G 5/02* (2013.01); *A61G 5/10* (2013.01); *A61N 1/0452* (2013.01);
(Continued)

(58) Field of Classification Search
CPC ........ A61G 5/02; A61G 5/10; A61G 2203/36; A61G 2210/00; A61N 1/36031;
(Continued)

(56) References Cited

U.S. PATENT DOCUMENTS 4,421,336 A * 12/1983 Petrofsky ............... A61G 5/023
180/6.5
2007/0049814 A1 3/2007 Muccio
(Continued)

FOREIGN PATENT DOCUMENTS

CN 201342193 Y * 11/2009
CN 205913475 U * 2/2017
(Continued)

OTHER PUBLICATIONS

"Revord, Percutaneous Electrical Nerve Stimulation and Electrical Nerve Stimulation and Electrical Muscle Stimulation. Spine-health. Apr. 21, 2017" (Year: 2017).*
(Continued)

*Primary Examiner* — Joseph M Dietrich
*Assistant Examiner* — Michael T. Holtzclaw
(74) *Attorney, Agent, or Firm* — Ballard Spahr LLP

(57) ABSTRACT

A system and method for improving stability of a wheelchair user includes a wheelchair having sensors measuring motion parameters to sense collisions and sharp turns which may unseat the user. Neuromuscular stimulating electrodes attached to extensor and flexor muscles of the user's trunk and under the command of a controller in communication with the sensors activate the muscles during turns and collisions to counteract the forces induced. A system and method for increasing manual propulsion efficiency includes sensors for sensing motion parameters indicating completion of a manual push of the wheelchair wheels and recovery from the push. Neuromuscular stimulating electrodes
(Continued)

attached to extensor and flexor muscles of the user's trunk and under the command of a controller in communication with the sensors activate the muscles at the appropriate time in the cycle of push and recovery.

28 Claims, 10 Drawing Sheets

(51) Int. Cl.
    *A61N 1/36*       (2006.01)
    *A61N 1/04*       (2006.01)
    *A61N 1/05*       (2006.01)
    *A61N 1/02*       (2006.01)
    *A61B 5/00*       (2006.01)

(52) U.S. Cl.
    CPC ....... *A61N 1/0456* (2013.01); *A61N 1/36003* (2013.01); *A61N 1/3606* (2013.01); *A61N 1/36014* (2013.01); *A61N 1/36031* (2017.08); *A61N 1/36139* (2013.01); *A61B 5/00* (2013.01); *A61G 2203/36* (2013.01); *A61G 2210/00* (2013.01); *A61N 1/025* (2013.01); *A61N 1/0476* (2013.01); *A61N 1/0504* (2013.01)

(58) Field of Classification Search
    CPC .............. A61N 1/0452; A61N 1/36139; A61N 1/36003; A61N 1/36014; A61N 1/3606; A61N 1/0456; A61N 1/0476; A61N 1/0504; A61N 1/025; A61B 5/00
    See application file for complete search history.

(56) References Cited

U.S. PATENT DOCUMENTS

| | | | |
|---|---|---|---|
| 2007/0123950 A1 | 5/2007 | Ludlow et al. | |
| 2009/0309344 A1* | 12/2009 | van Roosmalen | B60R 22/023 280/801.1 |
| 2010/0036456 A1* | 2/2010 | Mayr | A61N 1/36003 607/48 |
| 2011/0168478 A1 | 7/2011 | Kuo et al. | |
| 2013/0123568 A1* | 5/2013 | Hamilton | A61N 1/36017 600/13 |
| 2014/0031910 A1* | 1/2014 | Fisher | A61N 1/36003 607/118 |
| 2015/0374563 A1 | 12/2015 | Mussa-Ivaldi et al. | |
| 2016/0075226 A1* | 3/2016 | Biderman | B60L 15/025 301/6.5 |
| 2017/0231856 A1* | 8/2017 | Karlovich | A61N 1/36003 607/148 |
| 2018/0153430 A1* | 6/2018 | Ang | A61B 5/053 |

FOREIGN PATENT DOCUMENTS

| | | | | |
|---|---|---|---|---|
| DE | 3827153 C1 * | 8/1989 | ......... | A63B 71/0009 |
| WO | 9820827 | 5/1998 | | |
| WO | 2017059534 | 4/2017 | | |
| WO | WO-2017059534 A1 * | 4/2017 | ............... | G01C 9/06 |

OTHER PUBLICATIONS

Audu, M. et al. (2015). A neuroprosthesis for control of seated balance after spinal cord injury. Journal of neuroengineering and rehabilitation, 12, 8. https://doi.org/10.1186/1743-0003-12-8 (https://www.ncbi.nlm.nih.gov/pmc/articles/PMC4326199/) (Year: 2015).*
Patel, et al. "Wheelchair Neuroprosthesis for Improving Dynamic Trunk Stability," in IEEE Transactions on Neural Systems and Rehabilitation Eng., vol. 25, No. 12, pp. 2472-2479, Dec. 2017, doi: 10.1109/TNSRE.2017.2727072. pub date: Jul. 14, 2017.(https://ieeexplore.ieee.org/document/7981346?source=IQplus) (Year: 2017).*
Armstrong et al.; Automatic Application of Neural Stimulation During Wheelchair Propulsion After SCI Enhances Recovery of Upright Sitting from Destabilizing Events; (2018) Journal of NeuroEngineering and Rehabilitation; 13 pages.
Author Unknown; Spinal Cord Injury (SCI) Facts and Figures at a Glance; (2016) The National SCI Statistical Center (NSCISC).
Kamper et al.; Preliminary Investigation of the Lateral Postural Stability of Spinal Cord-Injured Individuals Subjected to Dynamic Perturbations; Spinal Cord (1999) vol. 37, pp. 40-46.

* cited by examiner

WHEELCHAIR SYSTEM WITH MOTION SENSORS AND NEURAL STIMULATION

CROSS REFERENCE TO RELATED APPLICATIONS

This application is based upon and claims priority to U.S. Provisional Application No. 62/541,879, filed Aug. 7, 2017 and hereby incorporated by reference.

FIELD OF THE INVENTION

This invention relates to wheelchairs having inertial sensors for providing information used to control neural stimulation of the wheelchair user.

BACKGROUND

For people with spinal cord injuries who have lost the ability to control their trunk muscles, minor disturbances, such as a sharp turn or a collision with a curb, can destabilize the user and cause a loss of erect sitting posture, potentially leading to injurious falls. Falls are in fact the leading cause of injury for wheelchair users, and account for over 66,000 wheelchair related injuries per year. The injuries can be serious and include lacerations, contusions, abrasions, fractures and can result in death. According to at least one survey of people having spinal cord injuries, trunk stability is among the top functions they would like to see restored. There is clearly an opportunity to improve the safety of wheelchair users by increasing trunk stability.

Loss of control of trunk muscles also reduces the efficiency of manual propulsion of wheelchairs. Wheelchair users with poor trunk control due to paralysis of core thigh, hip and trunk muscles have limited trunk stability and may be unable to fully or safely lean backward and forward, resulting in inefficient pushing of the wheelchair. The inability to efficiently propel the wheelchair can make traversing challenging terrain, such as inclined ramps, difficult and can also lead to shoulder injuries. There is clearly an opportunity to improve the efficiency of wheelchair propulsion by increasing or restoring a degree of trunk control.

SUMMARY

The invention concerns a wheelchair system providing neural stimulation to a user. In one example embodiment the system comprises a wheelchair. A sensor is positioned on the wheelchair for measuring a motion parameter thereof and generating one or more signals indicative of the motion parameter. A plurality of neural stimulating electrodes are attached to the user, each electrode attached to a respective muscle of the user for activating the respective muscle. A controller is in communication with the sensor and is adapted to receive the signals. The controller is also in communication with the plurality of electrodes for activating selected ones of the respective muscles in response to the signals.

The controller may be mounted on the wheelchair or the user. The motion parameter may comprise a linear motion parameter. The linear motion parameter is oriented in a direction of motion of the wheelchair and may be selected from the group consisting of linear velocity, linear acceleration and combinations thereof. The electrodes are attached to muscles selected from the group consisting of erector spinae, quadratus lumborum, gluteus maximus, posterior adductor and combinations thereof. The electrodes may be implanted beneath the user's skin or on a surface of the user's skin. The motion parameter may also comprise an angular motion parameter. The angular motion parameter is oriented about a turning axis of the wheelchair and may be selected from the group consisting of angular acceleration, angular velocity, and combinations thereof. The electrodes are attached to muscles selected from the group consisting of right erector spinae, right quadratus lumborum, right gluteus maximus, right posterior adductor, left erector spinae, left quadratus lumborum, left gluteus maximus, left posterior adductor and combinations thereof. The electrodes may be implanted beneath the user's skin or mounted on a surface of the user's skin.

In an example embodiment the sensor comprises an inertial measurement unit. Further by way of example, the sensor comprises at least one gyroscope and at least one accelerometer. In another example, the sensor comprises a radio frequency transmitter for wirelessly transmitting the signals to the controller. In an example embodiment the controller comprises a radio frequency receiver for receiving the signals and a microprocessor in communication with the receiver. In another example a seat belt controlled by a motor is mounted on the wheelchair. The controller controls the motor for tightening the belt. Further by way of example, a brake, controlled by an actuator, is mounted on the wheelchair, the controller controlling the actuator for applying the brake. In another example a distress indicator controlled by the controller for broadcasting a distress call.

The invention also encompasses a method of providing neural stimulation to a user of a wheelchair based upon motion of the wheelchair. In one example embodiment the method comprises:
  measuring a motion parameter of the wheelchair;
  generating a signal indicative of the motion parameter;
  evaluating the signal;
  activating at least one muscle of the user in response to the signal.

In one example, measuring the motion parameter comprises measuring a linear velocity of the wheelchair. By way of example, measuring the motion parameter comprises measuring a linear acceleration of the wheelchair or measuring an angular acceleration of the wheelchair or measuring an angular velocity of the wheelchair. By way of example, generating a signal comprises generating a signal indicative of at least one motion parameter selected from the group consisting of a linear velocity, a linear acceleration, an angular velocity, an angular acceleration, and combinations thereof. By way of example, evaluating the signal comprises converting the signal to a value indicative of a magnitude of the motion parameter and comparing the magnitude to a threshold magnitude of the motion parameter. In another example, evaluating the signal comprises converting the signal to a value indicative of a direction of the motion parameter and comparing the direction to a reference direction.

In an example embodiment, activating at least one muscle of the user in response to the signal comprises selecting one or more muscles of the user and applying a neural stimulus to activate the one or more muscles. By way of example, selecting one or more muscles of the user comprises selecting the erector spinae, quadratus lumborum, gluteus maximus, and posterior adductor muscles when the motion parameter is a linear acceleration which exceeds a threshold value. Further by way of example, selecting one or more muscles of the user comprises selecting right erector spinae, right quadratus lumborum, right gluteus maximus, and right posterior adductor muscles when the motion parameter is an angular acceleration or an angular velocity in a counter-clockwise direction about a turning axis. Also by way of example, selecting one or more muscles of the user comprises selecting left erector spinae, left quadratus lumborum, left gluteus maximus, and left posterior adductor muscles when the motion parameter is an angular acceleration or an angular velocity in a clockwise direction about a turning axis.

The invention also encompasses method of providing neural stimulation to a user of a wheelchair based upon motion of the wheelchair during a collision. In an example embodiment the method comprises:
- monitoring linear acceleration in a direction of motion of the wheelchair;
- calculating a moving root mean square of the linear acceleration and comparing it against a first predetermined threshold value;
- comparing a derivative of the root mean square linear acceleration against a second predetermined threshold value;
- calculating a change in velocity using the linear acceleration and comparing the change in velocity to a third predetermined threshold value;
- applying neuromuscular stimulation if the first, second and third predetermined threshold values are exceeded within a predetermined time period.

An example method of applying a restraint to a user of a wheelchair based upon motion of the wheelchair is also contemplated and comprises:
- measuring a motion parameter of the wheelchair;
- generating a signal indicative of the motion parameter;
- evaluating the signal;
- activating at least one the restraint in response to the signal.

By way of example, measuring the motion parameter comprises measuring a linear velocity of the wheelchair, measuring a linear acceleration of the wheelchair measuring an angular acceleration of the wheelchair or measuring an angular velocity of the wheelchair. In an example embodiment, generating a signal comprises generating a signal indicative of at least one the motion parameter selected from the group consisting of a linear velocity, a linear acceleration, an angular velocity, an angular acceleration, and combinations thereof.

In an example method, evaluating the signal comprises converting the signal to a value indicative of a magnitude of the motion parameter and comparing the magnitude to a threshold magnitude of the motion parameter. Also by way of example, evaluating the signal comprises converting the signal to a value indicative of a direction of the motion parameter and comparing the direction to a reference direction. Further by way of example, activating at least one restraint in response to the signal is selected from the group consisting of tightening a belt securing the user to the wheelchair, applying a brake to slow the wheelchair, broadcasting a distress signal and combinations thereof.

The invention further encompasses a system for providing assistance to a user for manual propulsion of a wheelchair. In one example embodiment the system comprises at least one sensor positioned on the user for measuring a motion parameter of the user while propelling the wheelchair. The at least one sensor generate one or more signals indicative of the motion parameter. A plurality of neural stimulating electrodes are positioned on the user, each electrode is attached to a respective muscle of the user for activating the respective muscle. A controller is in communication with the at least one sensor and adapted to receive the signals. The controller is also in communication with the plurality of electrodes for activating selected ones of the respective muscles in response to the signals. In one example embodiment the controller is mounted on either the wheelchair or the user. By way of examome, at least one sensor is mounted on the user in a position selected from the group consisting of an upper trunk of the user, a shoulder of the user, an arm of the user, a wrist of the user, a head of the user and combinations thereof. Further by way of example, the motion parameter is selected from the group consisting of a position of a part of the user, an acceleration of a part of the user, a rate of change of acceleration of a part of the user, an electrical potential of a muscle of the user, and combinations thereof. By way of example, the part of the user is selected from the group consisting of an upper trunk of the user, a shoulder of the user, an arm of the user, a wrist of the user, a head of the user and combinations thereof. In an example embodiment, the electrodes are attached to muscles selected from the group consisting of hip flexor muscles, hip extensor muscles, trunk flexor muscles, trunk extensor muscles, abdominal muscles and combinations thereof. By way of example, the electrodes are implanted beneath the user's skin or are mounted on a surface of the user's skin.

In an example embodiment, the at least one sensor comprises an inertial measurement unit. Further by way of example, the at least one sensor comprises at least one accelerometer. In another example, the at least one sensor comprises at least one electromyographic sensor. Also by way of example, the at least one sensor comprises a radio frequency transmitter for wirelessly transmitting the signals to the controller.

The invention also encompasses a method of providing assistance to a user for manually propelling a wheelchair. In one example embodiment, the method comprises:
- detecting when the user has recovered from a previous push of the wheels of the wheelchair;
- the user executing a next push of the wheels;
- applying neural stimulation to trunk and hip flexor muscles of the user while the user executes the next push of the wheels;
- detecting when the user has completed the next push of the wheels;
- removing neural stimulation to the trunk and the hip flexor muscles of the user when the user has completed the next push of the wheels;
- the user recovering from the next push of the wheels;
- applying neural stimulation to trunk and hip extensor muscles of the user while the user is recovering from the next push of the wheels;
- detecting when the user has recovered from the next push of the wheels;
- removing neural stimulation from the trunk and the hip extensor muscles of the user when the user has recovered from the next push of the wheels.

In an example embodiment, detecting when the user has recovered comprises measuring a motion parameter of a part of the user while the user is recovering. In an example embodiment, the motion parameter is selected from the group consisting of a position of a part of the user, an acceleration of a part of the user, a rate of change of acceleration of a part of the user, an electrical potential of a muscle of the user and combinations thereof. In an example embodiment, the part of the user is selected from the group consisting of an upper trunk of the user, a shoulder of the user, an arm of the user, a wrist of the user, a head of the user, and combinations thereof.

By way of example, detecting when the user has completed the push of the wheels comprises measuring a motion parameter of the user while the user is pushing the wheels. In an example embodiment, the motion parameter is selected from the group consisting of a position of a part of the user, an acceleration of a part of the user, a rate of change of acceleration of a part of the user, an electrical potential of a muscle of the user and combinations thereof. Further by way of example, the part of the user is selected from the group consisting of an upper trunk of the user, a shoulder of the user, an arm of the user, a wrist of the user, a head of the user, and combinations thereof. In an example embodiment, detecting when the user has recovered comprises measuring anterior-posterior acceleration of a wrist of the user. Further by way of example, the method comprises measuring a rate of change of the anterior-posterior acceleration. Also by way of example, the method comprises measuring a rate of change of a medial-lateral acceleration of the wrist. In an example embodiment, detecting when the user has completed the push comprises measuring anterior-posterior acceleration of a wrist of the user. By way of example, the method may also comprise measuring a rate of change of the anterior-posterior acceleration. An example embodiment further comprises measuring a medial-lateral acceleration of the wrist.

In an example embodiment, detecting when a user has completed a push of the wheels comprises:
- detecting an acceleration signal indicative of anterior-posterior acceleration of a part of the user greater than a predetermined threshold value;
- detecting an increasing rate of change of the acceleration signal;
- detecting a medial-lateral acceleration of the part of the user within a predetermined range of values.

By way of example, detecting when a user has recovered from a push of the wheels comprises:
- detecting an acceleration signal indicative of anterior-posterior acceleration of a part of the user less than a predetermined threshold value;
- detecting a decreasing rate of change of the acceleration signal;
- detecting a medial-lateral acceleration of the part of the user having an increasing rate of change.

In an example embodiment, the part of the user comprises a wrist.

DETAILED DESCRIPTION

Figure 1:
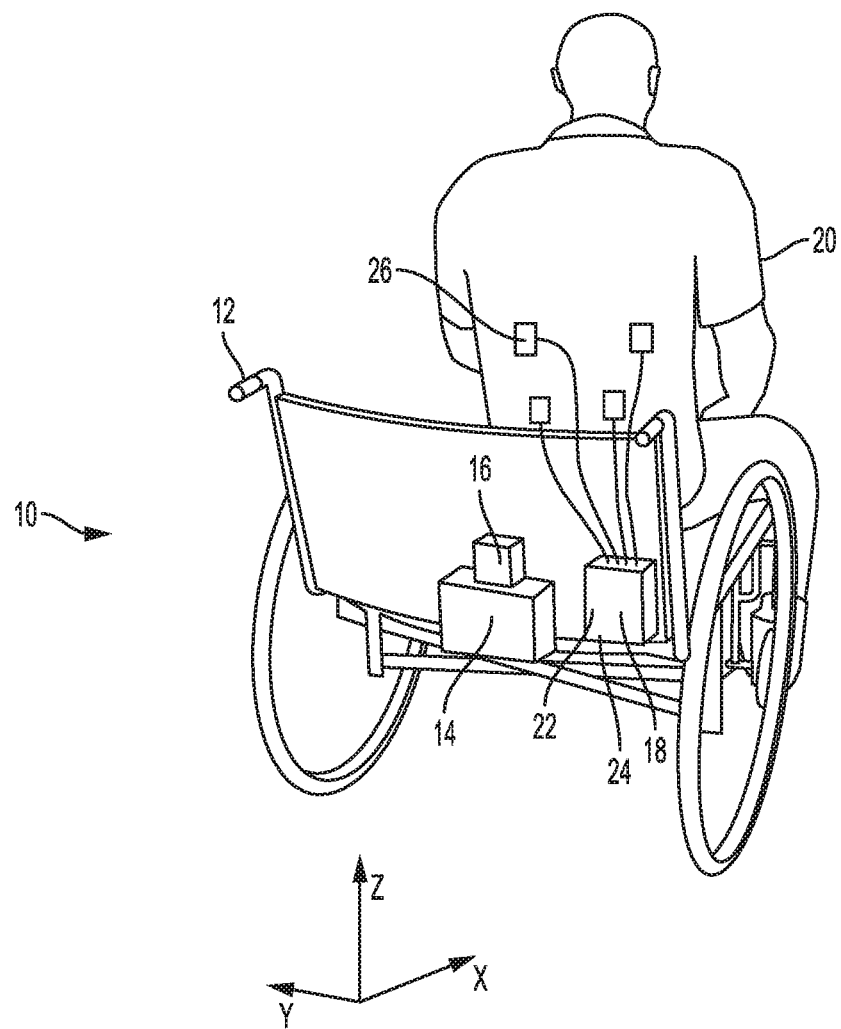
FIG. 1 is an isometric rear view of an example wheelchair system for stabilizing a user according to the invention.
Figure 2:
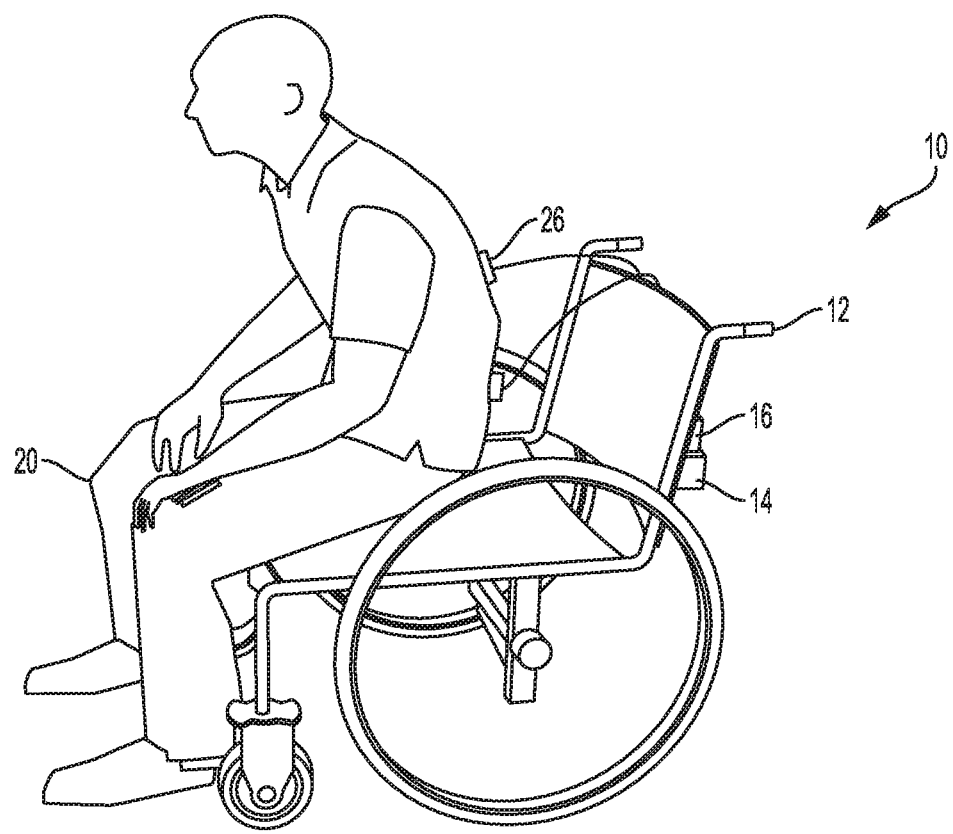
FIG. 2 is an isometric side view of the wheelchair system shown in FIG. 1.

FIGS. 1 and 2 show an example embodiment of a wheelchair system 10 according to the invention. System 10 comprises a wheelchair 12. A motion sensor 14 is positioned on the wheelchair 12. Motion sensor 14 measures one or more motion parameters of wheelchair 12 and generates signals indicative of the motion parameters. In an example embodiment the sensor 14 may be an inertial measurement unit (IMU) including accelerometers for measuring motion parameters such as acceleration of the wheelchair 12 in three mutually perpendicular axes (X, Y and Z as defined in FIG. 1) as well as one or more gyroscopes for measuring motion parameters such as angular velocity and angular acceleration of the wheelchair about the axes X, Y and Z. The sensor 14 also includes a radio frequency transmitter 16 used to transmit the signals wirelessly. A controller 18 is also part of system 10. In this example the controller 18 is also mounted on the wheelchair 12 but in another embodiment may be worn by (mounted on) the user 20. In the example embodiment shown controller 18 comprises a radio frequency receiver 22 for receiving signals from the sensor 14, and a microprocessor 24 in communication with receiver 22. The microprocessor may be, for example, a programmable logic controller. Software resident in the microprocessor 24 evaluates the signals from the sensor 14 and directs the microprocessor to issue commands to one or more of a plurality of neural stimulating electrodes 26, also part of system 10. Communication between controller 18 and electrodes 26 may be via wires or wirelessly.

Electrodes 26 are attached to respective muscles (detailed below) of the user 20 and selected ones are activated in response to the signals according to algorithms encoded in the software in the microprocessor 24. Electrodes 26 can be mounted on the surface skin of the user 20 using transcutaneous electrical nerve stimulation equipment (TENS) or implanted beneath the skin, using intramuscular implants or nerve cuff electrodes. In an experimental setting, an example system 10 used 8, 12 or 16 channel IPGs to deliver asymmetrical charged-balanced current controlled stimulus waveforms with pulse amplitudes (0-20 mA) selectable for each channel and variable pulse durations (0-250 μsec) and frequencies (0-20 Hz) set on a pulse by pulse basis.

The wheelchair system 10 according to the invention helps prevent user 20 from falling out of wheelchair 12 when unexpected destabilizing events, such as collisions or sharp turns, are encountered during everyday activities. This goal is accomplished by using the controller 18 to stimulate and thereby activate selected muscles and muscle groups (over which user 20 has lost control due to a spinal cord injury) in response to the motion parameters measured by sensor 14 and evaluated by algorithms in the software of the controller 18. When activated, the selected muscles restore trunk stability appropriately in response to the particular destabilizing event.

For collisions, such as when the wheelchair 12 encounters a curb, a linear motion parameter in the direction of wheelchair motion is used to determine muscle activation. Example linear motion parameters used by the controller 18 and measured by sensor 14 may be linear velocity, linear acceleration, or a combination of the two. The selected muscles to be activated by electrodes 26 in response to a collision are selected from knee, hip and trunk extensor muscles and include the erector spinae, the quadratus lumborum, the gluteus maximus, the posterior adductor and combinations thereof.

For sharp turns, an angular motion parameter oriented about a turning axis (axis Z in FIG. 1) of wheelchair 12 is used to determine muscle activation. Example angular motion parameters used by the controller and measured by sensor 14 include angular acceleration, angular velocity, and combinations of the two. The selected muscles to be activated by electrodes 26 in response to a sharp turn are again selected from knee, hip and trunk extensor muscles, but are separated laterally, with the right erector spinae, right quadratus lumborum, right gluteus maximus, and right posterior adductor muscles being selected when the motion parameter is an angular acceleration or an angular velocity in a counterclockwise direction about the Z axis, and the left erector spinae, left quadratus lumborum, left gluteus maximus, and left posterior adductor muscles being selected when the motion parameter is an angular acceleration or an angular velocity in a clockwise direction about the Z axis.

Figure 3:
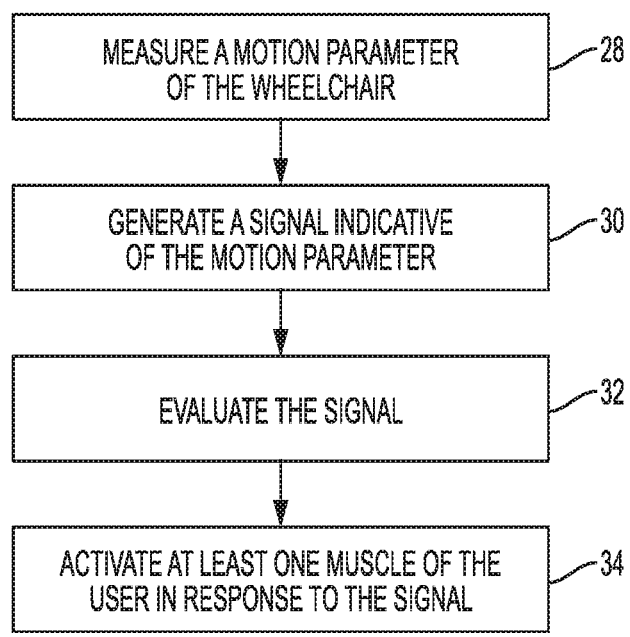
FIG. 3 is a flow chart illustrating an example method of stabilizing a user according to the invention.

The invention also encompasses a method of providing neural stimulation to the user 20 of wheelchair 12. FIG. 3 shows a flowchart illustrating an example method, which comprises:

measuring a motion parameter of the wheelchair (28);
generating a signal indicative of the motion parameter (30);
evaluating the signal (32); and
activating at least one muscle of the user in response to the signal (34).

As noted above, measuring the motion parameter of the wheelchair 12 includes measuring a linear acceleration and/or linear velocity (for a collision for example) and measuring the angular velocity and/or angular acceleration of the wheelchair about a turning axis (for sharp turns for example). Generating a signal includes generating a signal, for example, a voltage signal, indicative of any of the motion parameters including a linear velocity, a linear acceleration, an angular velocity, an angular acceleration, and combinations thereof.

Evaluating the signal for a collision event comprises converting the signal to a value indicative of the magnitude of the motion parameter and then comparing that magnitude to a known threshold value at which muscle stimulus should be applied. Effective threshold values are known from experiment to vary with each wheelchair user, and in experimental applications of the method, collision acceleration thresholds ranging from 3.05 g to about 3.76 g were identified for determining when muscle stimulus should be applied to the extensor muscles to resist forward flexion to stabilize the user and assist return to upright sitting during the collision.

For a turning event, evaluating the signal required determining the direction of the turn as well as its magnitude. Determining the turn direction comprises comparing the measured direction to a reference direction to determine whether to activate the left or right muscle groups. Experimental angular motion parameter magnitude thresholds for determining when to apply the muscle stimulus ranged from about 97 degrees/sec to about 100 degrees/sec for applying muscle stimulation during turns.

The step of activating at least one muscle, the muscle or muscle group is selected based upon the measured motion parameters and the neural stimulus is applied to the selected muscles appropriate for the event (collision or turn). As noted above for an example embodiment, the erector spinae, quadratus lumborum, gluteus maximus, and posterior adductor muscles are selected when the measured motion parameter is a linear acceleration (indicating a collision) which exceeds a threshold value. For a measured angular motion parameter indicating a left turn and which exceeds a threshold value, one or more muscles comprises the right erector spinae, the right quadratus lumborum, the right gluteus maximus, and the right posterior adductor muscles are selected. For a measured angular motion parameter indicating a right turn and which exceeds a threshold value, one or more muscles comprising the left erector spinae, the left quadratus lumborum, the left gluteus maximus, and the left posterior adductor muscles are selected.

Figure 4:
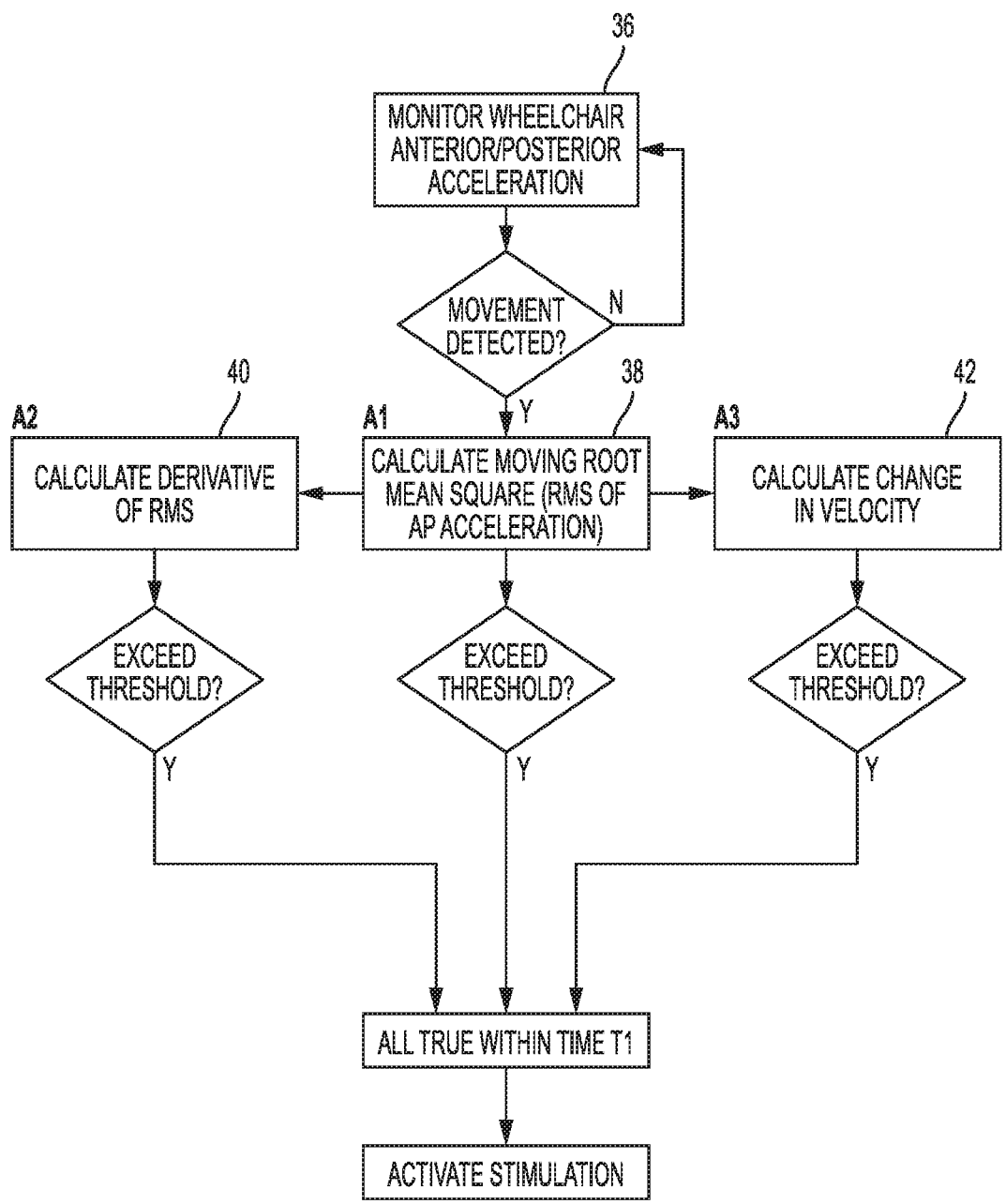
FIG. 4 is a flow chart illustrating an example method of stabilizing a user according to the invention.

FIG. 4 illustrates a detailed example method according to the invention used during a collision. In this example, the linear acceleration in the direction of motion of the wheelchair (axis X, anterior/posterior acceleration) is monitored (36) using the sensor 14 and controller 18. Once motion is detected, algorithms 38, 40 and 42 within the controller 18 begin monitoring the signals from the sensor 14 to detect a collision. Algorithm 38 calculates the moving root mean square of the anterior/posterior acceleration continually and compares it against a threshold. Algorithm 40 compares the derivative of the RMS anterior/posterior acceleration against a threshold. Algorithm 42 calculates the change in velocity (integral of acceleration) and compares that to a threshold. If the thresholds are exceeded within a predetermined time period, T1, then a crash has occurred and the appropriate neuromuscular stimulation is applied by the controller 18 via electrodes 26.

Figure 5:
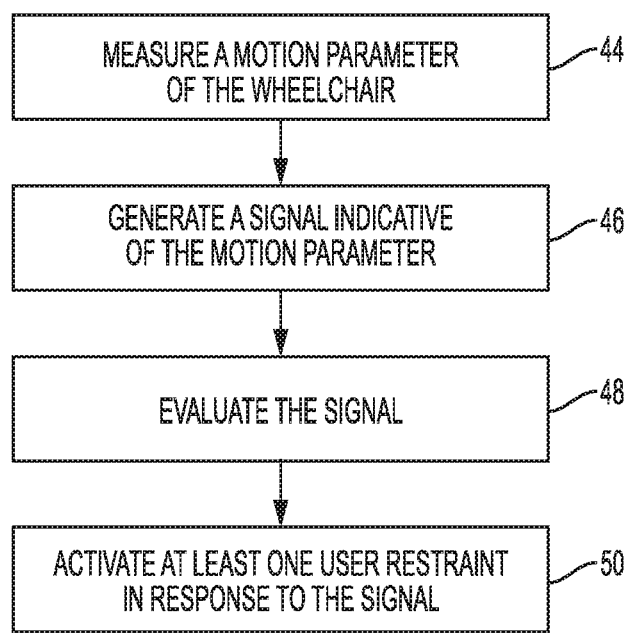
FIG. 5 is a flow chart illustrating an example method of stabilizing a user according to the invention.

FIG. 5 illustrates another example embodiment of the method according to the invention which comprises the steps of:

measuring a motion parameter of the wheelchair (44);
generating a signal indicative of the motion parameter (46);
evaluating the signal (48); and
activating at least one user restraint in response to the signal (50).

Figure 6:
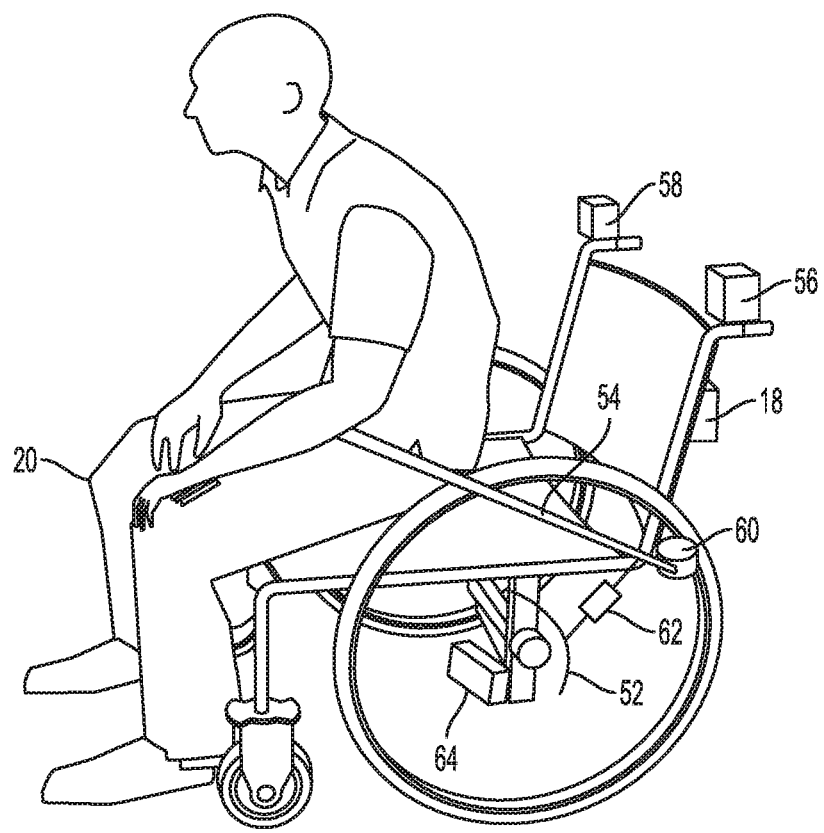
FIG. 6 is an isometric side view of another example embodiment of a wheelchair system for stabilizing a user according to the invention.

The method steps are similar to those for applying neuromuscular stimulation as described above, the difference being that a mechanical restraint is applied instead of muscular stimulation. As shown in FIG. 6 the restraints may include applying a brake 52, tightening a seat belt 54 to restrain user 20, and/or broadcasting a distress signal from a speaker 56 or over a radio frequency transmitter 58. Activation of the various restraints is effected by the controller 18 via appropriate interfaces, such as a servomotor 60 to tighten the seat belt, or an actuator 62, such as a solenoid, to apply the brake. The various mechanical devices used with the system 10 are advantageously electrical, to permit the system to be operated by a battery 64.

Figure 7:
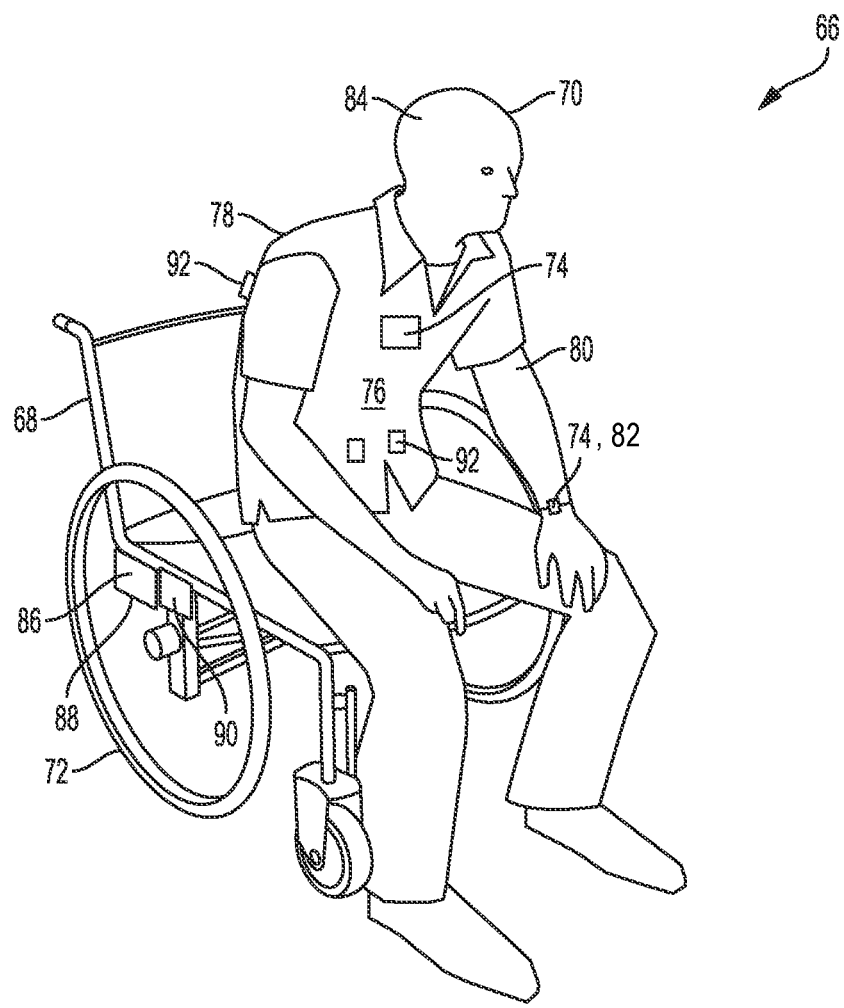
FIG. 7 is an isometric front view of an example embodiment of a wheelchair system for increasing propulsion efficiency of a user according to the invention.

FIG. 7 shows another system 66 which improves the efficiency of manually propelled wheelchairs 68. System 66 is advantageous for users 70 with poor trunk control due to paralysis of core, thigh, hip and trunk muscles. Such users have limited trunk stability and are either unable to fully lean backward and forward when pushing the wheels 72 or are unsafe when doing so. This condition leads to inefficient pushing and thus difficulty in traversing challenging terrain such as inclined ramps.

System 66 comprises at least one sensor 74 positioned on user 70 for measuring a motion parameter of the user while the user is propelling the wheelchair 68. Motion parameters which are useful in system 66 include a position of a part of the user, an acceleration of a part of the user, a rate of change of acceleration of a part of the user as well as an electrical potential of a muscle of the user. One or more sensors 74 may be advantageously positioned on the user's upper trunk 76, shoulder 78, arm 80, in particular wrist 82, and head 84 for measuring the motion parameters of one or more of these parts of user 70. When it is desired to use electrical potential of a muscle as a motion parameter it is advantageous to use an electromyographic sensor mounted on the shoulder 78. Sensor 74 generates one or more signals indicative of the motion parameter while the user is propelling wheelchair 68.

In this example embodiment, one motion sensor 74 is used. Sensor 74 comprises a tri-axial accelerometer, such as a commercially available activity tracker, and is worn on the wrist 82. The wrist accelerometer 74 has a radiofrequency transmitter which transmit the signals indicative of the selected motion parameters wirelessly to a controller 86. Controller 86 may be worn by (mounted on) the user 70 or mounted on the wheelchair 68 (shown). In the example embodiment shown, controller 86 comprises a radiofrequency receiver 88 for receiving signals from the sensors 74, and a microprocessor 90 in communication with receiver 88. The microprocessor may be, for example, a programmable logic controller. Software resident in the microprocessor 90 evaluates the signals from the sensors 74 and directs the microprocessor to issue commands to one or more of a plurality of neural stimulating electrodes 92, also part of system 66.

Electrodes 92 are attached to respective muscles (detailed below) of the user 70 and selected ones are activated in response to the signals according to algorithms encoded in the software in the microprocessor 90. Electrodes 92 can be mounted on the surface skin of the user 70 using transcutaneous electrical nerve stimulation equipment (TENS) or implanted beneath the skin, using intramuscular implants or nerve cuff electrodes. Selected muscles on which electrodes 92 are to be attached for neuromuscular stimulation to improve propulsion efficiency include hip flexor muscles, hip extensor muscles, trunk flexor muscles, trunk extensor muscles, abdominal muscles and combinations thereof.

Figure 8:
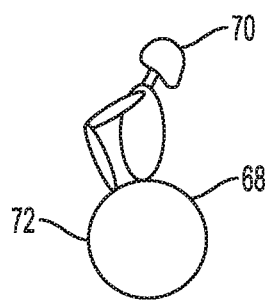
FIGS. 8-14 are schematic representations showing stages in the cycle of a user propelling the wheelchair system shown in FIG. 7.
Figure 9:
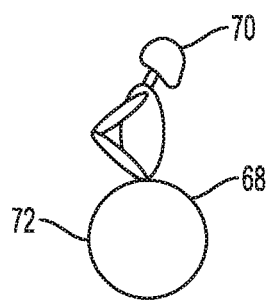
Figure 10:
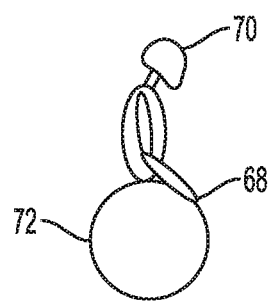
Figure 11:
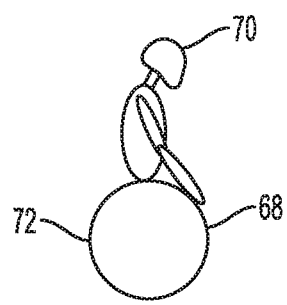
Figure 12:
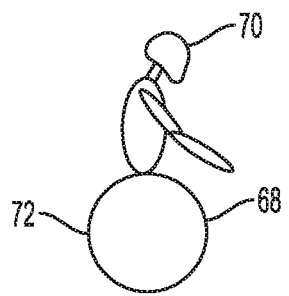
Figure 13:
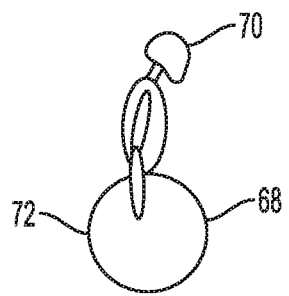
Figure 14:
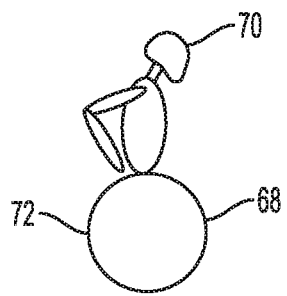

The invention further encompasses a method of providing assistance to user 70 for manually propelling wheelchair 68. An example method is illustrated in FIGS. 8-14, and comprises:

detecting when user 70 has recovered from a previous push of the wheels 72 of the wheelchair 68 (FIG. 8);
user 70 executing a next push of the wheels 72 (FIGS. 9-11);
applying neural stimulation to trunk and hip flexor muscles of user 70 while the user executes the next push of the wheels;
detecting when the user has completed the next push of the wheels (FIG. 11);
removing neural stimulation to the trunk and hip flexor muscles of user 70 when the user has completed the next push of said wheels (FIG. 11);
the user 70 recovering from the next push of said wheels (FIGS. 12-14);
applying neural stimulation to trunk and hip extensor muscles of the user 70 while the user is recovering from the next push of the wheels (FIGS. 12-14);
detecting when the user 70 has recovered from the next push of the wheels (FIG. 8);
removing neural stimulation from the trunk and the hip extensor muscles of the user 70 when the user has recovered from the next push of the wheels (FIG. 8).

As illustrated in FIGS. 8-14, it is advantageous to apply neuromuscular stimulation to the trunk and hip flexor muscles while user 70 executes a push of wheels 72 because the pushing effort of the arms 80 is augmented by the force and weight of the trunk 76 as it bends forward in flexion (FIGS. 9-11) in response to the stimulation. Similarly, it is advantageous to remove the stimulation to the trunk and hip flexor muscles and apply stimulation to the trunk and hip extension muscles to cause extension of the trunk 76 (FIGS. 12-14) so that the user 70 may recover in preparation for the next push (FIG. 8). The timing of the application and removal of the neuromuscular stimulation depends upon detecting when user 70 has recovered and when the user has completed a push.

Detecting when user 70 has recovered from a push is effected by measuring a motion parameter of a part of the user while recovering. Practical motion parameters include a position of a part of the user, an acceleration of a part of the user, a rate of change of acceleration of a part of the user and an electrical potential of a muscle of the user, as well as combinations of these motion parameters. The parts of the user for which these motion parameters may be measured include the upper trunk 76, the shoulder 78, the arm 80, the wrist 82, the head 84 and combinations of these parts.

Detecting when user 70 has completed a push is effected by measuring a motion parameter of a part of the user while the user is pushing the wheels 72. Practical motion parameters include a position of a part of the user, an acceleration of a part of the user, a rate of change of acceleration of a part of the user and an electrical potential of a muscle of the user, as well as combinations of these motion parameters. The parts of the user for which these motion parameters may be measured include the upper trunk 76, the shoulder 78, the arm 80, the wrist 82, the head 84 and combinations of these parts.

Figure 15:
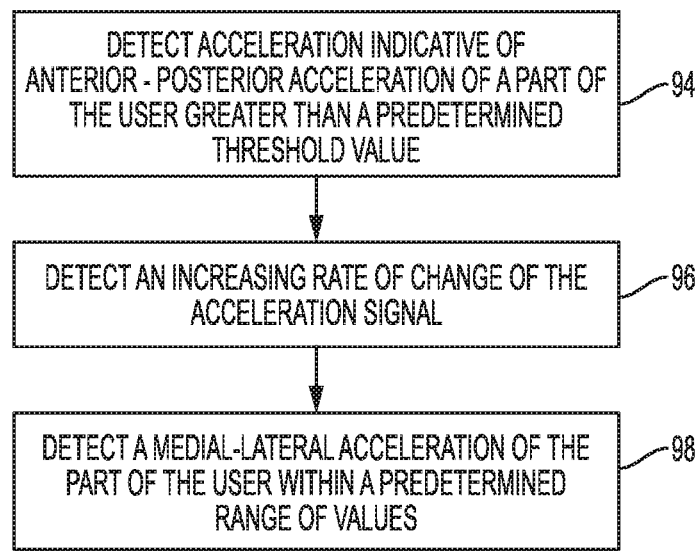
FIG. 15 is a flow chart illustrating an example method of increasing the propulsion efficiency of a wheelchair according to the invention.
Figure 16:
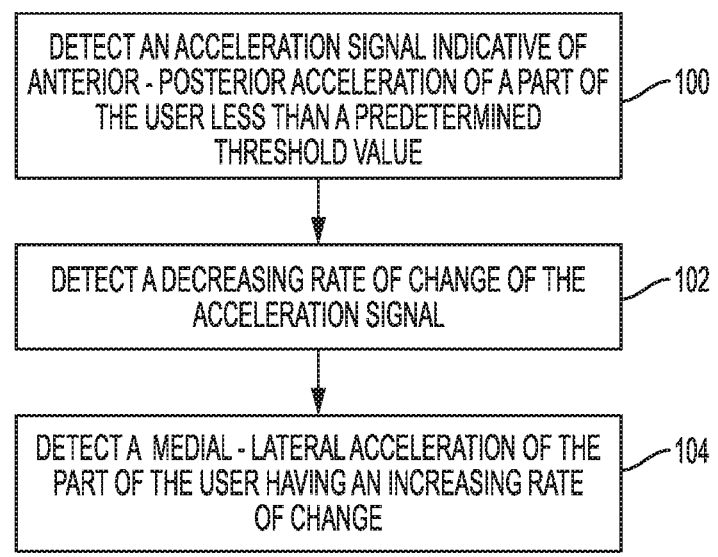
FIG. 16 is a flow chart illustrating an example method of increasing the propulsion efficiency of a wheelchair according to the invention.

Experimental evidence has shown that motion parameters of the wrist 82 of user 70, specifically the anterior-posterior acceleration and rate of change of acceleration, in combination with medial-lateral acceleration and rate of change of acceleration of the wrist, are useful in determining both the recovery from a push and the completion of a push by the user. FIGS. 15 and 16 illustrate an example embodiment of an algorithm using these wrist motion parameters.

As shown in FIG. 15, detecting when user 70 has completed a push of wheels 72 is effected by:

detecting an acceleration signal indicative of anterior-posterior acceleration of a part of the user (wrist 82) greater than a predetermined threshold value (94);
detecting an increasing rate of change of the acceleration signal (96);
detecting a medial-lateral acceleration of the part of the user (wrist 82) within a predetermined range of values (98).

As shown in FIG. 16, detecting when user 70 has recovered from a push is effected by:

detecting an acceleration signal indicative of anterior-posterior acceleration of a part of the user (wrist 82) less than a predetermined threshold value (100);
detecting a decreasing rate of change of the acceleration signal (102);
detecting a medial-lateral acceleration of the part of the user (wrist 82) having an increasing rate of change (104).

Although it is expected that the motion parameters of other parts of the user 70 may also be used to detect push completion and recovery, it has been found effective to use the motion of the wrist 82 of the user 70 to execute this algorithm.

It is expected that the systems and methods according to the invention will enhance a wheelchair user's experience, ability, efficiency and safety.

What is claimed is:

1. A wheelchair system providing neural stimulation to a user, said system comprising:
   a wheelchair;
   an inertial measurement unit positioned on said wheelchair for measuring a motion parameter of said wheelchair and generating one or more signals indicative of said motion parameter;
   a plurality of neural stimulating electrodes, each said electrode configured to be attached to a respective muscle of said user for activating said respective muscle;
   a controller in communication with said inertial measurement unit and adapted to receive said signals, said controller also being in communication with said plurality of electrodes configured for activating selected ones of said respective muscles in response to said signals;
   wherein said inertial measurement unit comprises at least one gyroscope and said motion parameter comprises an angular motion parameter.

2. The wheelchair system according to claim 1, wherein said controller is mounted on one of said wheelchair or said user.

3. The wheelchair system according to claim 1, wherein said inertial measurement unit comprises at least one accelerometer and said motion parameter comprises a linear motion parameter.

4. The wheelchair system according to claim 3, wherein said linear motion parameter is oriented in a direction of motion of said wheelchair, said linear motion parameter being selected from the group consisting of linear velocity, linear acceleration and combinations thereof.

5. The wheelchair system according to claim 4, wherein said electrodes are configured to be attached to said muscles selected from the group consisting of erector spinae, quadratus lumborum, gluteus maximus, posterior adductor and combinations thereof.

6. The wheelchair according to claim 5, wherein said electrodes are configured to be implanted beneath skin of said user.

7. The wheelchair according to claim 5, wherein said electrodes are configured to be mounted on a surface of skin of said user.

8. The wheelchair system according to claim 1, wherein said angular motion parameter is oriented about a turning axis of said wheelchair, said angular motion parameter being selected from the group consisting of angular acceleration, angular velocity, and combinations thereof.

9. The wheelchair system according to claim 8, wherein said electrodes are configured to be attached to said muscles selected from the group consisting of right erector spinae, right quadratus lumborum, right gluteus maximus, right posterior adductor, left erector spinae, left quadratus lumborum, left gluteus maximus, left posterior adductor and combinations thereof.

10. The wheelchair system according to claim 9, wherein said electrodes are configured to be implanted beneath skin of said user.

11. The wheelchair system according to claim 9, wherein said electrodes are configured to be mounted on a surface of skin of said user.

12. The wheelchair system according to claim 1, wherein said inertial measurement unit comprises a radio frequency transmitter for wirelessly transmitting said signals to said controller.

13. The wheelchair system according to claim 1, wherein said controller comprises a radio frequency receiver for receiving said signals and a microprocessor in communication with said receiver.

14. The wheelchair system according to claim 1, further comprising a seat belt controlled by a motor mounted on said wheelchair, said controller controlling said motor for tightening said belt.

15. The wheelchair system according to claim 1, further comprising a brake controlled by an actuator mounted on said wheelchair, said controller controlling said actuator for applying said brake.

16. The wheelchair system according to claim 1, further comprising a distress indicator controlled by said controller for broadcasting a distress call.

17. A method of providing neural stimulation to at least one muscle of a user of a wheelchair based upon motion of said wheelchair, said method comprising:
   measuring a motion parameter of said wheelchair using an inertial measurement unit;
   generating a signal indicative of said motion parameter;
   evaluating said signal;
   generating a stimulus configured to activate said at least one muscle of said user in response to said signal;
   wherein said inertial measurement unit comprises at least one gyroscope and said motion parameter comprises an angular motion parameter.

18. The method according to claim 17, wherein said measuring said motion parameter comprises measuring a linear velocity of said wheelchair.

19. The method according to claim 17, wherein said measuring said motion parameter comprises measuring a linear acceleration of said wheelchair.

20. The method according to claim 17, wherein said measuring said motion parameter comprises measuring an angular acceleration of said wheelchair.

21. The method according to claim 17, wherein said measuring said motion parameter comprises measuring an angular velocity of said wheelchair.

22. The method according to claim 17, wherein said generating a signal comprises generating a signal indicative of at least one said motion parameter selected from the group consisting of a linear velocity, a linear acceleration, an angular velocity, an angular acceleration, and combinations thereof.

23. The method according to claim 17, wherein said evaluating said signal comprises:
   converting said signal to a value indicative of a magnitude of said motion parameter; and
   comparing said magnitude to a threshold magnitude of said motion parameter.

24. The method according to claim 17, wherein said evaluating said signal comprises:
   converting said signal to a value indicative of a direction of said motion parameter; and
   comparing said direction to a reference direction.

25. The method according to claim 17, wherein said generating said stimulus in response to said signal comprises:

selecting said one or more muscles of said user;
activating an electrode configured to apply a neural stimulus configured to activate said one or more muscles.

26. The method according to claim 25, wherein said selecting said one or more muscles of said user comprises selecting erector spinae, quadratus lumborum, gluteus maximus, and posterior adductor muscles when said motion parameter is a linear acceleration which exceeds a threshold value.

27. The method according to claim 25, wherein said selecting said one or more muscles of said user comprises selecting right erector spinae, right quadratus lumborum, right gluteus maximus, and right posterior adductor muscles when said motion parameter is an angular acceleration or an angular velocity in a counterclockwise direction about a turning axis.

28. The method according to claim 25, wherein said selecting said one or more muscles of said user comprises selecting left erector spinae, left quadratus lumborum, left gluteus maximus, and left posterior adductor muscles when said motion parameter is an angular acceleration or an angular velocity in a clockwise direction about a turning axis.

* * * * *